United States Patent [19]

Kum

[11] Patent Number: 4,907,579
[45] Date of Patent: Mar. 13, 1990

[54] DISPOSABLE ADHESIVE BANDAGE

[75] Inventor: Kwang N. Kum, Sinkikun, Japan

[73] Assignee: Tsuneharu Noguchi, Fukuoka, Japan

[21] Appl. No.: 217,665

[22] Filed: Jul. 12, 1988

[30] Foreign Application Priority Data

Feb. 8, 1988 [KR] Rep. of Korea ............... 88-1460

[51] Int. Cl.⁴ .................................. A61L 15/00
[52] U.S. Cl. ........................... 128/156; 128/155;
128/888; 128/893; 128/894; 604/304; 604/307
[58] Field of Search ............... 128/155, 91 R, 888,
128/83, 90, 115.1, 893, 894, 156; 604/304, 307

[56] References Cited

U.S. PATENT DOCUMENTS

| 706,250 | 8/1902 | Müller | 2/2 X |
|---|---|---|---|
| 2,344,021 | 3/1944 | Bouziane . | |
| 2,785,677 | 5/1953 | Stumpf | 128/156 |
| 3,119,390 | 1/1964 | Levitt | 128/894 |
| 3,304,938 | 2/1967 | Perkins, Jr. | 128/156 |
| 3,565,075 | 2/1971 | Jerry | 604/307 |
| 3,782,377 | 1/1974 | Rychuk | 604/307 X |
| 3,783,869 | 1/1974 | Schnipper . | |
| 4,126,130 | 11/1978 | Cowden et al. | 128/156 X |
| 4,192,300 | 3/1980 | Devers | 128/155 |
| 4,212,296 | 7/1980 | Schaar | 128/156 |
| 4,285,338 | 8/1981 | Lemelson | 128/155 |
| 4,297,995 | 11/1981 | Golub | 128/156 |
| 4,646,731 | 3/1987 | Brower . | |
| 4,667,666 | 5/1987 | Fryslie | 128/156 |
| 4,675,009 | 6/1987 | Hymes et al. . | |
| 4,695,277 | 9/1987 | Lauk | 604/304 |
| 4,747,841 | 5/1988 | Kuratomi et al. | 604/304 X |
| 4,787,888 | 11/1988 | Fox | 604/304 X |

Primary Examiner—Richard J. Apley
Assistant Examiner—N. Paul
Attorney, Agent, or Firm—Birch, Stewart, Kolasch & Birch

[57] ABSTRACT

A disposable adhesive bandage which includes a rigid base member, an absorbent pad disposed on the base member, an adhesive strip being coated on the absorbent pad, an aperture disposed in the adhesive strip, and a protective backing sheet for covering the adhesive strip whereby, when the bandgage is adhered to a human body around a wounded area caused by an injection or the like, the aperture is positioned directly over the wounded area and the adhesive portion of the bandage does not adhere to the wounded area of the human body.

5 Claims, 2 Drawing Sheets

DISPOSABLE ADHESIVE BANDAGE

BACKGROUND OF THE INVENTION

1. Field of the Invention

The present invention relates to an improved disposable adhesive bandage and more particularly, to a disposable adhesive plaster containing a pad for stopping bleeding after a blood transfusion, a blood collection, or an injection, or the like for the human body.

2. Prior Art of the Invention

Many types of devices for stopping bleeding are known in the art. For example, adhesive bandages having a plurality of apertures which communicate with an adhesive bandage pad, sterilized gauzes, and absorbent sanitary cottons are used to stop the bleeding after an injection or the like. However, such devices for stopping bleeding suffer from many problems. For example, when such a device includes an adhesive portion, the adhesive portion may contact the wound portion of the human body. On the contrary, when such a device does not have an adhesive portion, the device cannot effectively adhere to the wound area. Also, since the conventional bandage has a flexible bandage strip, when a protecting backing sheet is removed from the flexible base strip, the bandage develops a wrinkled face so that it is difficult to attach it to the human body.

SUMMARY OF THE INVENTION

Accordingly, it is an object of the present invention to provide an improved disposable bandage for stopping bleeding after an injection, or the like for the human body.

Another object of the present invention is to provide a disposable adhesive plaster which includes an absorbent pad disposed on a base, an adhesive strip, and an aperture disposed in the center of the adhesive strip for mating with an injected portion of the human body to directly contact with the absorbent pad. Therefore, the absorbent pad can sufficiently absorb the blood for stopping bleeding and preventing the adhesive strip from contacting the injected portion of the human body.

A further object of the present invention is to provide a disposable adhesive plaster having a adhesive strip and a base member which are made of a rigid material, respectively, for preventing the plaster from developing a wrinkled face when a protective backing sheet is removed from the adhesive strip.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a disposable adhesive bandage which includes a rigid base member, an absorbent pad disposed on the base member, an adhesive strip disposed on the absorbent pad, an aperture disposed in the adhesive strip, and a protective backing sheet for covering the adhesive strip whereby, when the bandage adheres to the human body after the injection, or the like, the aperture mates with the injected portion and the adhesive strip does not adhere to the injected portion of the human body.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENT

Figure 1:
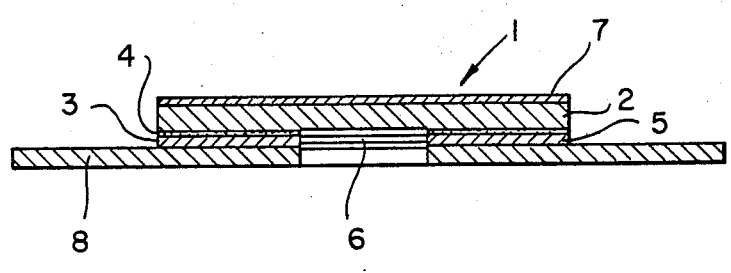
FIG. 1 is a sectional view of a disposable adhesive bandage of the present invention.
Figure 5:
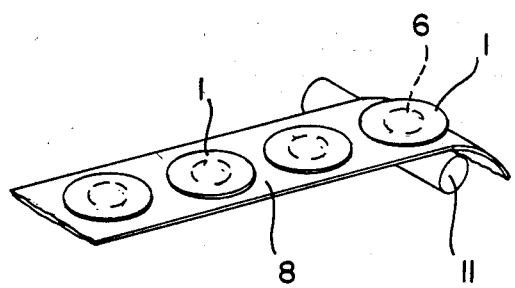
FIG. 5 is a perspective view of the disposable adhesive bandage of the present showing separating each bandage from a protective backing sheet.

Referring now in detail to the drawings for the purpose of illustrating preferred embodiments of the present invention, the disposable adhesive bandage 1 as shown in FIGS. 1 and 5 comprises a rigid base member 7, an absorbent pad 2 disposed on the rigid base member 7, a rigid adhesive strip 5 coated by adhesives 3 and 4, an aperture 6 disposed in the center of the rigid adhesive strip 5, and a protective backing sheet 8 adhered to the rigid strip by the adhesive 3. The rigid base member 7 is made of an opaque plastic material. The absorbent pad 2 is made of any suitable sterile sheet material such as textile fabric, for example, a non-woven fiber. The rigid strip 5 is made of a polyethylene terephthalate. The aperture 6 has a diameter of about 7 mm.

In use, the disposable adhesive bandage 1 can be easily removed from the protective backing sheet 8 by using a roller 11. The separated bandage 1 can adhere to the human body for stopping bleeding after an injection by positioning the aperture 6 over the injected portion and so that blood is sufficiently absorbed through the absorbent pad 2. On the other hand, the disposable adhesive bandage can effectively adhere to the human body by adhering through the adhesive 4 to the area around the injected portion.

Methods of manufacturing the disposable adhesive bandage 1 of the present invention include the following, for example.

Figure 2:
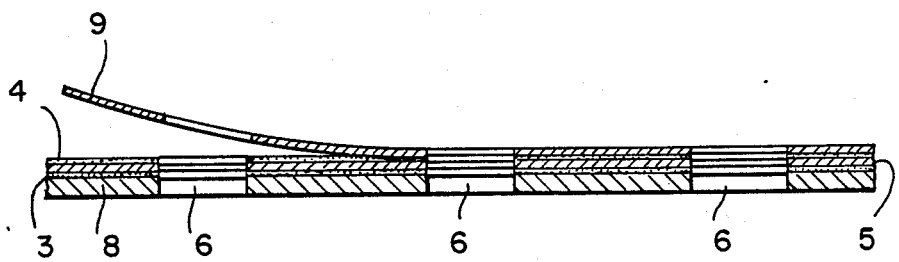
FIGS. 2 and 3 are a sectional view of the disposable adhesive bandage of the present invention showing a method of manufacturing the bandage.
Figure 3:
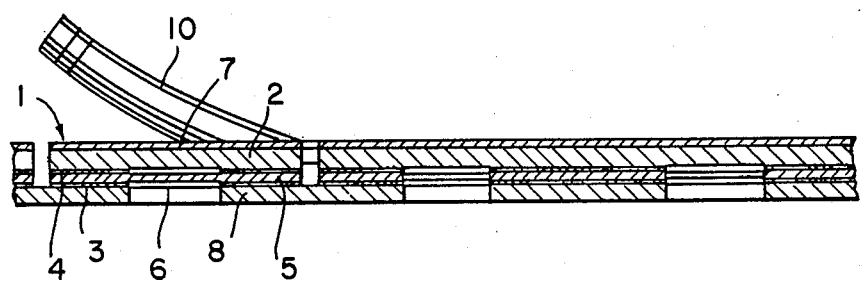
Figure 4:
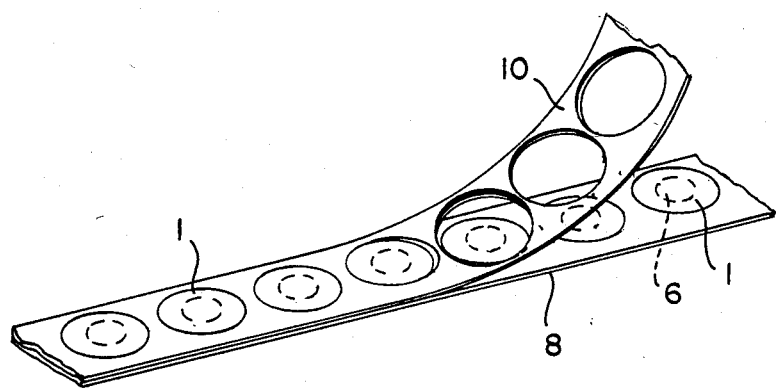
FIG. 4 is a perspective view of the disposable adhesive bandage of the present invention showing an additional embodiment of the method of manufacturing the bandage.

As shown in FIGS. 2 and 3, first the rigid strip 5 is attached to the protective backing sheet 8 at the adhesive 3 and to a processing removal sheet 9 at the adhesive 4. Thereafter, the plurality of apertures 6 are formed by punching with a small tubular machine (not shown) which has a diameter equal to that of aperture 6 (FIG. 2).

Second, the absorbent pad 2 containing the rigid base member 7 replaces the processing removal sheet 9. Thereafter, a large tubular punching machine having an annular punching portion, which has a larger diameter than that of the punching machine used to punch the aperture 6, is used to alternately punch the base member 7, pad 2, and strip 5 about the apertures 6 so as to leave punched remnants 10 (FIG. 3).

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A disposable adhesive bandage for stopping bleeding from an external wound of a human body which comprises:

a rigid base member, an absorbent pad disposed on said rigid base member, a rigid strip having an aperture disposed in the center thereof and a first adhesive and a second adhesive being coated on both surfaces thereof, said rigid strip being adhered to said absorbent pad by the first adhesive, and a protective backing sheet adhered to said rigid strip by the second adhesive whereby after the removal of the protective backing sheet, the bandage is directly attached to the human body over the external wound so that aperture is positioned directly over said external wound.

2. The disposable adhesive bandage of claim 1, wherein the base member is made of an opaque plastic material.

3. The disposable adhesive bandage of claim 1, wherein the absorber pad is made of a non-woven fiber.

4. The disposable adhesive bandage of claim 1, wherein the rigid strip is made of a polyethylene terephthate.

5. The disposable adhesive bandage of claim 1, wherein the aperture has a diameter of about 7 mm.

* * * * *